US008067496B2

(12) United States Patent  
Zech et al.

(10) Patent No.: US 8,067,496 B2
(45) Date of Patent: Nov. 29, 2011

(54) CURABLE SILICONE IMPRESSION MATERIALS WITH HIGH TEAR STRENGTH AND LOW CONSISTENCY

(75) Inventors: Joachim W. Zech, Kaufering (DE); Franziska Strauss, Utting (DE); Henning Hoffmann, Windach (DE); Peter Bissinger, Diessen (DE); Wolf Steiger, Geretsried (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/046,068

(22) Filed: Mar. 11, 2011

(65) Prior Publication Data

US 2011/0160332 A1    Jun. 30, 2011

Related U.S. Application Data

(63) Continuation of application No. 10/554,989, filed as application No. PCT/EP2004/004861 on May 7, 2004.

(30) Foreign Application Priority Data

May 9, 2003  (EP) ..................................... 03010519

(51) Int. Cl.
C08L 83/00 (2006.01)
C08L 83/04 (2006.01)
C08F 283/00 (2006.01)

(52) U.S. Cl. .......................... 524/588; 524/862; 525/478
(58) Field of Classification Search .................. 524/588, 524/862; 525/478
See application file for complete search history.

(56) References Cited

U.S. PATENT DOCUMENTS

| | | | |
|---|---|---|---|
| 3,661,744 A | 5/1972 | Kehr et al. | |
| 3,715,334 A | 2/1973 | Karstedt | |
| 3,775,352 A | 11/1973 | Leonard, Jr. | |
| 3,814,730 A | 6/1974 | Karstedt | |
| 3,933,880 A | 1/1976 | Bergstrom et al. | |
| 3,957,713 A | 5/1976 | Jeram et al. | |
| 4,035,453 A | 7/1977 | Hittmair et al. | |
| 4,096,159 A | 6/1978 | Hechtl et al. | |
| 4,273,902 A | 6/1981 | Tomioka et al. | |
| 4,340,709 A | 7/1982 | Jeram et al. | |
| 4,359,565 A * | 11/1982 | Puppe et al. | 528/15 |
| 4,461,854 A | 7/1984 | Smith | |
| 4,600,731 A | 7/1986 | Louis et al. | |
| 4,609,687 A | 9/1986 | Schwabe et al. | |
| 4,614,758 A | 9/1986 | Schwabe et al. | |
| 4,657,959 A | 4/1987 | Bryan et al. | |
| 4,759,633 A | 7/1988 | Schmid | |
| 4,806,575 A | 2/1989 | Waller et al. | |
| 4,845,164 A * | 7/1989 | Gutek | 528/15 |
| 4,877,854 A | 10/1989 | Hattori et al. | |
| 4,879,339 A | 11/1989 | Yoshino et al. | |
| 4,882,398 A * | 11/1989 | Mbah | 525/478 |
| 4,891,400 A | 1/1990 | Schwabe et al. | |
| 4,957,667 A | 9/1990 | Hamer | |
| 5,082,886 A | 1/1992 | Jeram et al. | |
| 5,086,148 A | 2/1992 | Jochum et al. | |
| 5,276,110 A | 1/1994 | Zhou et al. | |
| 5,286,105 A | 2/1994 | Herold et al. | |
| 5,371,162 A * | 12/1994 | Konings et al. | 528/15 |
| 5,403,885 A | 4/1995 | Voigt et al. | |
| 5,415,544 A | 5/1995 | Oxman et al. | |
| 5,426,200 A | 6/1995 | Dauth et al. | |
| 5,569,691 A | 10/1996 | Guggenberger et al. | |
| 5,573,189 A | 11/1996 | Ward et al. | |
| 5,661,222 A | 8/1997 | Hare | |
| 5,677,410 A | 10/1997 | Mager et al. | |
| 5,679,755 A | 10/1997 | Mager et al. | |
| 5,684,060 A | 11/1997 | Konings et al. | |
| 5,750,589 A | 5/1998 | Zech et al. | |
| 5,830,951 A | 11/1998 | Fiedler | |
| 5,848,894 A | 12/1998 | Rogers | |
| 5,849,812 A | 12/1998 | Zech et al. | |
| 5,863,965 A | 1/1999 | Hare | |
| 5,922,795 A | 7/1999 | McDermott et al. | |
| 5,955,513 A | 9/1999 | Hare | |
| 6,012,610 A | 1/2000 | Pauser et al. | |
| 6,040,354 A | 3/2000 | Hubner et al. | |
| 6,121,362 A | 9/2000 | Wanek et al. | |
| 6,121,368 A | 9/2000 | Heying et al. | |
| 6,124,407 A | 9/2000 | Lee et al. | |
| 6,169,155 B1 | 1/2001 | Alvarez et al. | |
| 6,184,407 B1 | 2/2001 | Yoshitake | |
| 6,201,055 B1 | 3/2001 | Lutz et al. | |
| 6,225,433 B1 | 5/2001 | Isshiki et al. | |
| 6,239,244 B1 | 5/2001 | Stepp et al. | |
| 6,244,740 B1 | 6/2001 | Wagner et al. | |
| 6,313,190 B1 | 11/2001 | Bublewitz et al. | |
| 6,335,412 B1 | 1/2002 | Okamoto et al. | |

(Continued)

FOREIGN PATENT DOCUMENTS

| | | |
|---|---|---|
| CA | 1284399 | 5/1991 |
| CA | 1285682 | 7/1991 |
| DE | 2646726 A1 | 4/1978 |
| DE | 3406233 A1 | 8/1985 |
| DE | 3409139 A1 | 9/1985 |
| DE | 3741575 A1 | 6/1988 |
| DE | 4122310 A1 | 1/1993 |
| DE | 4306997 A1 | 9/1994 |
| DE | 4324685 A1 | 1/1995 |
| DE | 19517838 A1 | 11/1996 |

(Continued)

OTHER PUBLICATIONS

A. W. van der Made and P.W.N.M. van Leeuwen, Silane Dendrimers, J. Chem. Soc. Commun. (1992), p. 1400-1401.
A. W. van der Made and P.W.N.M. van Leeuwen, Dendrimeric Silanes, Adv. Mater. (1993), 5, No. 6, p. 466 ff.
D. Seyferth lo and D.Y. Son, Synthesis of an Organosilicon Dendrimer Containing 324 SI-H Bonds, Organometallics (1994), 13, pp. 2682-2690.

(Continued)

*Primary Examiner* — Robert Loewe

(74) *Attorney, Agent, or Firm* — Pamela L. Stewart

(57) ABSTRACT

The invention relates to curable silicone compositions which contain silane based crosslinkers and a mixture of different organopolysiloxanes. The compositions are particularly suitable as curable impression materials in dental applications.

16 Claims, No Drawings

U.S. PATENT DOCUMENTS

| | | |
|---|---|---|
| 6,335,413 B1 | 1/2002 | Zech et al. |
| 6,552,104 B1 | 4/2003 | Hare |
| 6,559,199 B1 | 5/2003 | Pusineri et al. |
| 6,642,184 B1 | 11/2003 | De Ridder |
| 6,677,393 B1 * | 1/2004 | Zech et al. .......... 524/366 |
| 6,998,427 B2 * | 2/2006 | Del Torto et al. .......... 523/109 |
| 7,005,460 B2 | 2/2006 | Bublewitz et al. |
| 7,186,758 B2 | 3/2007 | Zech et al. |
| 2001/0016609 A1 | 8/2001 | Meguriya et al. |
| 2002/0156186 A1 | 10/2002 | Bublewitz et al. |
| 2002/0193502 A1 * | 12/2002 | Hare .......... 524/588 |
| 2002/0197214 A1 | 12/2002 | Bublewitz et al. |
| 2003/0181624 A1 | 9/2003 | Kashiwagi et al. |
| 2004/0110863 A1 * | 6/2004 | Zech et al. .......... 523/109 |
| 2004/0122142 A1 | 6/2004 | Meguriya |
| 2004/0132947 A1 | 7/2004 | Achenbach et al. |
| 2005/0006794 A1 | 1/2005 | Kashiwagi et al. |
| 2005/0059776 A1 | 3/2005 | Cray et al. |
| 2005/0147275 A1 | 7/2005 | Powell et al. |
| 2005/0159522 A1 | 7/2005 | Bublewitz et al. |

FOREIGN PATENT DOCUMENTS

| | | |
|---|---|---|
| DE | 19603242 A1 | 11/1996 |
| DE | 29606895 U1 | 7/1997 |
| DE | 19719438 A1 | 11/1997 |
| DE | 19730515 A1 | 1/1999 |
| DE | 10103446 | 8/2002 |
| DE | 10112904 A1 | 10/2002 |
| DE | 20121446 U1 | 11/2002 |
| EP | 0152887 A2 | 8/1985 |
| EP | 0158141 A2 | 10/1985 |
| EP | 166107 A2 | 1/1986 |
| EP | 0188880 A2 | 7/1986 |
| EP | 0219660 A2 | 4/1987 |
| EP | 0231420 B1 | 8/1987 |
| EP | 0263039 A1 | 4/1988 |
| EP | 0268347 B1 | 5/1988 |
| EP | 0480238 B1 | 4/1992 |
| EP | 0743313 A2 | 11/1996 |
| EP | 0891763 A2 | 1/1999 |
| EP | 0993863 A2 | 4/2000 |
| EP | 1652889 A1 | 5/2006 |
| FR | 2781808 A1 | 4/2000 |
| GB | 2196638 | 5/1988 |
| WO | WO 87/03001 A1 | 5/1987 |
| WO | WO 96/08230 A1 | 3/1996 |
| WO | WO 96/12754 A1 | 5/1996 |
| WO | WO 96/32088 A1 | 10/1996 |
| WO | WO 97/37632 A1 | 10/1997 |
| WO | WO 97/40102 A | 10/1997 |
| WO | WO 99/09934 A2 | 3/1999 |
| WO | WO 00/59453 A1 | 10/2000 |
| WO | WO 02/058641 A1 | 8/2002 |
| WO | WO-02078647 A1 * | 10/2002 |

OTHER PUBLICATIONS

DIN 50125, 1991.
DIN 51048-1—superseded by DIN EN 993-7, 1980.
DIN 51048-2—superseded by DIN EN 993-6, 1995.
DIN 53018-1, 1976.
DIN 53453, 1997.
DIN 53455—superseded by EN ISO 527-1 and 527-2, 1996.
DIN 53505, 2000.
Encyclopedia of Polymer Science and Engineering, 2nd edition, vol. 15, pp. 204-308, 1989.
International Encyclopedia of Composites (S. M. Lee, publisher, vol. 2, VCH-Verlagsgesellschaft, New York 1990, p. 182).
International Standard, ISO 4823, "Dentistry-Elastomeric Impression Materials", Title page, Publication page, Table of Contents, Forward page, and pp. 1-34 (38 pp. Total), 2001.
J. Burghardt, Chemie und Technologie der Polysiloxane in "Silikone, Chemie und Technologie", Vulkan Verlag, Essen, 1989, pp. 23-37.
L. Ehrnford, Dental Composites Reinforced With Microporous Sintered Glassfiber Networks, (Swed. Dent. J. Suppl. 18, 1983).
"Liquid Injection Molding: Processing guide for Silastic® Liquid Silicone rubber (LSR) and Silastic® Fluoro Liquid Silicone Rubber (F-LSR)," Dow Corning: Rubber Fabric Solutions, Midland, MI; 31 pgs. (2008).
McCabe, Applied Dental Materials, 7th Edition, Blackwell Scientific Publ., Oxford, England, Title page, Publ. Page, and p. 114 (1999).
Urdang, *The Random House College Dictionary*, New York, NY, 1973; cover page, title page and p. 1280 only; 3 pgs.
W. Noll, Chemistry and Technology of Silicones, Academic Press, New York and London, Title page, Publication page, Table of Contents, and Chapter 4 (pp. 124-189) (72 pages in total), 1968.
W. Noll, "Chemie und Technologie der Silikone", Verlag Chemie Weinheim, 2 edition, 1964, pp. 162-206, Ch 5.
W. Noll, "Chemie und Technologie der Silikone", Verlag Chemie Weinham, 1968, p. 212 ff, Ch 6.

* cited by examiner

CURABLE SILICONE IMPRESSION MATERIALS WITH HIGH TEAR STRENGTH AND LOW CONSISTENCY

CROSS REFERENCE TO RELATED APPLICATIONS

This is a continuation of application Ser. No. 10/554,989, filed Sep. 18, 2006; which was a national stage filing under 35 U.S.C. 371 of PCT/EP2004/004861 filed May 7, 2004, which International Application was published by the International Bureau in English on Nov. 18, 2004, which claims priority to EP 03010519.1, filed May 9, 2003, the disclosure of which is incorporated by reference in their entirety herein.

The invention relates to curable silicone compositions which contain silane based crosslinkers and a mixture of different organopolysiloxanes. The compositions are particularly suitable as curable impression materials in dental applications, especially as wash impression materials.

For dental materials, there is a high demand for materials with high tear strength for various indications. While high tear strength of the cured product plays an important role and is desirable in almost every type of curable material for dental applications, differences apply with regard to the hardness of the cured material and the viscosity of the uncured precursors.

Materials for bite registration, temporary and permanent filling materials, crown and bridge materials as well as cement and enamel can be named as examples for materials where high tear strength, high hardness and a fairly high viscosity of the precursor materials is desirable. The end hardness plays an important role in all of the above uses, for example it determines the dimensional stability, cuttability and castability of impression materials.

The situation is different, however, with regard to impression materials for securing a precise representation of oral hard and soft tissue to support and enable subsequent preparation of crowns, bridges, dentures and other oral prostheses. Generally, any material designed for utilization in one or more of the above mentioned fields of dentistry has to allow for the best possible structural reproduction of details of oral hard and soft tissue in order to enable detail fidelity in the preparation of oral prosthetic work.

Owing to different circumstances connected with the use of a curable material in the field of bite registration, temporary and permanent filling materials, crown and bridge materials as well as cement and enamel and the use of a curable material in the field of impression materials for securing a precise representation of oral hard and soft tissue, requirements for the precursors as well as for the cured materials are different.

In employing polyorganosiloxanes as dental impression materials, a number of difficulties have arisen. First of all, tear strength tends to be low. For effectively taking an impression, it is necessary to be able to easily remove the impression from the dentition without tearing, particularly at thin marginal areas, to preserve fine detail. In the past, fillers of various types have been added to improve tear strength. Such additions may result in some improvement, but such improvements have proved inadequate with respect to an increase in viscosity.

Because of the rheological behavior of most conventional two component hydrophilic silicones, high yield stresses can be observed in such compounds. To provide for low forces for releasing the material, large static mixers for mixing the two components prior to their use have to be employed. This, however, results in a high rate of waste because much of the material often remains in the large mixer. Therefore, it is desirable to achieve a low yield stress of both, the single components and the mix, in order to minimize the force which is necessary to remove the paste from the cartridge.

With conventional so-called light body formulations a high stress has to be applied to obtain a flow of the impression material into the fine details of the preparation. Low viscosity type materials ("light bodies") are therefore often used in combination with a high viscosity type material in the so called "putty/wash" technique or in the "double mix" technique. Especially for imprints taken with the above mentioned "putty/wash" technique, tear strength is important for the wash-material, since this material is responsible for preserving the finest details of the imprint. However, many imprint materials as available according to the prior art show a tendency to tear under stress, especially under stress developing when a cured imprint is removed from a difficult area of a dental preparation in the oral cavity, e.g., a preparation involving bridges. Such a tendency to tear can result in loss of important details of the imprint, thus leading to inferior oral prosthetic work.

To remedy the problems described above, the prior art concentrates on the use of vinyl groups carrying QM-resins or VQM-resins carrying vinyl groups. The letters Q and M stand for quadrifunctional and monofunctional monomers, which constitute the resins. Generally, such QM or VQM-resins can be described as reaction products of a reaction between quadrifunctional silicones and vinyl groups carrying monofunctional silicones, where the term "functionality" relates to the number of functional groups resulting in the formation of a Si—O—Si-Bond during reaction. Depending on the relation of quadrifunctional elements and monofunctional elements, the number of vinyl groups in the reaction product varies and generally increases with an increasing amount of quadrifunctional elements.

Hare in U.S. Pat. No. 5,661,222 and U.S. Pat. No. 5,955,513 and Fiedler in U.S. Pat. No. 5,830,951 describe two component polymerizable polyorganosiloxane compositions for use in making dental impressions. The described compositions show an improved tear strength which, according to Hare and Fiedler, results from inclusion of a quadrifunctional polysiloxane having a vinyl content of 0.16 to 0.24 mmole/g. The composition also contains a surfactant with an HLB of 8-11, resulting, according to Hare and Fiedler, in a contact angle with water of less than 50° after 3 minutes.

The above mentioned formulations, however, suffer from several disadvantages. The dripping consistency of the materials described in the above mentioned prior art is often low, which can result in problems when taking imprints from the upper jaw. A low dripping consistency can result in a loss of curable material and loss of detail or insufficient tear strength in locations where the amount of material is too low.

A further disadvantage of the formulations as described in the prior art is the use of VQM-resins in amounts of at least 20 wt.-%, based on the amount of polyorganosiloxane. This high amount of polyfunctional elements in the curable composition results in a number of drawbacks as compared to conventional formulations. While the tear strength may improve due to the introduction of such polyfunctional elements, the possibility to prepare "tailor-made" compositions is diminished, since the chemical nature of a large amount of the formulation is fixed. The tailoring of curable impression materials with desirable properties, however, largely depends on the possibility of the developer to influence these properties with a maximal degree of freedom in his choice of constituents. This is especially important for influencing properties such as end hardness and rheological behavior, which often depends on filler materials which may be present in impression materials in large quantities.

Another important aspect of light and ultra light body materials is the consistency of such materials with regard to dripping. Often, light or ultra light body materials show a tendency to drip off the preparation site resulting in a loss of material and, consequently, in a loss of detail of the impression Zech in U.S. Pat. No. 6,335,413 describes curable dental impression materials containing organopolysiloxanes carrying olefinically unsaturated double bonds and silane dendrimers. According to Zech, the use of silane dendrimers results in an increased hardness for cured materials containing the above mentioned constituents. The formulations described by Zech are, e.g., useful as bite registrates with a high shore D-formulations described by Zech give relatively brittle materials and are, e.g., useful as bite registrates with a high shore D hardness. The elasticity of the described materials is, however, insufficient for a use in impression materials since the maximum elongation is smaller than 50%.

Zech in WO 02/078647 describes a curable dental impression material containing organopolysiloxanes carrying olefinically unsaturated double bonds. The document describes the use of a mixture of organopolysiloxanes with two different viscosities. The disclosed materials, however, exhibit a consistency of less than or equal to 35 mm according to ISO 4823.

Due to the above mentioned deficiencies of formulations known from the prior art there is a high demand for curable organopolysiloxane containing formulations that overcome the these deficiencies.

It is thus an object of the present invention, to provide a formulation for the preparation of elastomers with good tear strength after curing without sacrificing a major part of the consituents of the formulation for crosslinking monomers. It is another object of the present invention to provide curable organopolysiloxane containing formulations that give elastomers with good tear strength upon curing where the formulations have an improved dripping consistency. It is another object of the present invention to provide curable organopolysiloxane containing formulations that yield elastomers with good tear strength after curing where the formulations have a viscosity which enables the use of such formulations as light body or ultra light body wash materials for taking impressions, especially impressions from within the oral cavity.

One or more of the above objects are achieved by curable materials as described in the following text.

Surprisingly, it has been found that adding silanes with at least two alkenyl groups to curable materials containing at least a mixture of two organopolysiloxanes A1 and A2 wherein the value for the viscosity of A2 is different from the value for the viscosity of A1 increases the tear strength of these materials considerably, simultaneously acts against the decrease in consistency value according to ISO 4823 of the non-cured materials, and allows for a maximum of freedom of formulation to provide impression materials with tailor made properties.

The present invention thus relates to a curable material comprising:
(A) at least two different types of organopolysiloxanes A1 and A2 with at least two ethylenically unsaturated groups per molecule,
(B) organohydrogenpolysiloxanes with at least 3 SiH groups per molecule,
(C) optionally organopolysiloxanes without reactive groups,
(D) a catalyst for promoting the reaction between A and B
(E) optionally hydrophilizing agents,
(F) fillers,
(G) optionally conventional dental additives, adjuvants and colorants and
(H) at least one silane with at least two alkenyl groups per molecule,
wherein the at least two different types of organopolysiloxanes A1 and A2 with at least two ethylenically unsaturated groups per molecule have a different viscosity and the consistency of the curable material according to ISO 4823 is >35 mm or >40 mm or >43 mm.

Component A according to the present invention generally contains organopolysiloxanes with at least two pendant or terminal triorganosiloxy groups of which at least one of the three organic groups is a group with an ethylenically unsaturated double bond. Generally, the groups with an ethylenically unsaturated double bond can be located at any monomeric unit of the organopolysiloxane. It is, however, preferred, when the groups with an ethylenically unsaturated double bond are located on or at least near the terminal monomeric units of the polymer chain of the organopolysiloxane. In another preferred embodiment at least two of the groups with an ethylenically unsaturated double bond are located on the terminal monomeric units of the polymer chain.

The term "monomeric units" as used throughout the present text relates to repeating structural elements in the polymer that form the polymer backbone, unless expressly stated otherwise.

Preferred organopolysiloxanes of this general structure are represented by the following formula I:

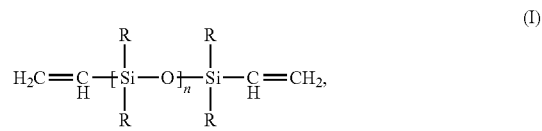

in which the radicals R can be selected independently from each other and represent a non-substituted or substituted monovalent hydrocarbon group with 1 to 6 C atoms, which is preferably free from aliphatic multiple bonds and n is generally chosen such that the viscosity of the organopolysiloxanes lies between 4 and 100,000 mPas or between 6 and 50,000 mPas.

Generally, the radicals R can represent any non-substituted or substituted monovalent hydrocarbon group with 1 to 6 C atoms. Corresponding non-substituted or substituted monovalent hydrocarbon group with 1 to 6 C atoms can be linear or, if the number of Carbon atoms exceeds 2, branched or cyclic. Generally, the radicals R can be equipped with all types substituents that do not interfere with at least one of the remaining consituents of the composition and do not interfere with the curing reaction. The term "interfere" as used in the context of the present text relates to any influence of such a subsituent on at least one of the remaining consituents of the composition or the curing reaction, or both, which is detrimental to the properties of the hardened product. The term "detrimental" as used in the context of the present text relates to a change of properties of the precursors or the cured product that affect the usefulness of the precursors or the cured product related to the intended use of the precursors or the cured product in a negative manner.

In another preferred embodiment of the present invention at least 50% of the radicals R represent methyl groups. Examples of other R radicals that can be present in the organopolysiloxanes according to formula I are ethyl, propyl, isopropyl, n-butyl, tert.butyl, the pentyl isomers, the hexyl isomers, vinyl, propenyl, isopropenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples of such molecules are described in U.S. Pat. No. 4,035,453, the disclosure of which, especially the disclosure of the latter document regarding the above mentioned molecules, their chemical constitution and their preparation, is expressly regarded as being part of the disclosure of the present document and is incorporated herein by reference.

The preparation of molecules of the above mentioned formula I is generally known to the skilled person. The preparation of corresponding molecules can be achieved, e.g., according to standard procedures which are portrayed in W. Noll, "Chemie und Technologie der Silikone", Verlag Chemie Weinheim 2. edition 1964, pages 162-206 or J. Burghardt, Chemie und Technologie der Polysiloxane in "Silikone, Chemie und Technologie", Vulkan Verlag, Essen, 1989, pages 23-37.

Linear polydimethylsiloxanes of the above structure with the specified viscosity ranges for which the end groups consist of dimethylvinylsiloxy units and the other radicals R in the chain consist of methyl groups are particularly preferred.

Component A, as described above, according to the present invention consists of at least two different constituents A1 and A2. It is within the context of the present invention that Component A consists of more than two different constituents, e.g., of 3, 4, 5, 6, 7, 8, 9 or 10 or more constituents which would the be labelled A3, A4, A5, A6, A7, A8, A9 and A10 up to An for the $n^{th}$ constituent of n constituents overall.

In order to achieve the advantages of the present invention, at least two of the constituents constituting component A have to differ in their viscosity, preferably by a factor of at least 2. This means that in the material according to the invention, of the different types of organopolysiloxanes as constituents of component A, at least A1 and A2 have a different viscosity and the value for the viscosity of A2 is preferably at least twice as high as the value for the viscosity of A1 for the same type of viscosity measurement.

The term "constituents" as used herein with regard to the constituents of component A relates to organopolysiloxanes differing at least in their average weight molecular weight, related to their polydispersity after preparation, to a measurable extent. The present invention thus does not regard polymers of different chain lengths as obtained within a process for the preparation of one type of polymer within the achieved polydipersity of the chosen method as different constituents, under the proviso that the method of preparation results in a monomodal dispersion of polymer chain lengths.

The difference in viscosities is preferably higher than a factor of 2, e.g., a factor of 5, 10, 20, 30, 40, 50, 60, 70, 80, 90 or 100. The difference in viscosities can be even higher, e.g., 200, 300, 500, 800, 1000 or 5000, it should, however, not exceed a value of about 10000. It should be kept in mind that the values mentioned above relate to a factor for the difference in viscosities, not the viscosity values themselves.

It is another preferred embodiment of the present invention when the constituent of A with the lowest viscosity of all constituents of A has a viscosity in the range of about 10 to about 7000 mPas, or about 10 to about 2000, or about 10 to about 1000 or about 50 to about 500 mPas or about 100 to about 300 mPas. A most preferred constituent of A with the lowest viscosity has a viscosity in the range of about 150 to about 250 mPas.

In another preferred embodiment of the present invention the constituent of A with the highest viscosity of all constituents of A has a viscosity of about 500 to about 45000 mPas, e.g. from about 1000 to about 30000 mPas or about 3000 to about 15000 mPas. Good results can be achieved when the constituent of A with the highest viscosity of all constituents of A has a viscosity of about 4000 to about 10000 mPas, e.g. from about 5000 to about 9000 mPas or about 6000 to about 8000 mPas.

In another preferred embodiment of the present invention, the component A comprises at least three constituents A1, A2 and A3. In this case, the above mentioned definition for the relation of the viscosities of the constituent with the highest viscosity and the constituent with the lowest viscosity, A3 and A1, is also applicable. The remaining constituent A2 can generally have any viscosity with a value between the values for viscosity of A1 and A3. It is, however, preferred, if the value for the viscosity of A2 is less than half of the value for the viscosity of A3 and more than double the value of the viscosity of A1. In another preferred embodiment of the present invention, the viscosity of constituent A2 (in a combination of three constituents A1, A2 and A3) is between about 500 and about 10.000, especially between about 1000 and about 5000 or between about 1500 and about 3000.

It is thus also a preferred embodiment according to the present invention, if the component A comprises at least 3 constituents A1, A2 and A3 with different viscosity values, A1 having the lowest viscosity value and A3 having the highest viscosity value.

It is furthermore preferred when the number of constituents in component A is 2 to about 5, especially 2, 3 or 4. The number of 2 constituents, A1 and A2, or 3 constituents A1, A2 and A3 is most preferred.

A preferred method of measurement, however, is performed with Haake Rotovisco RV20 (spindle MV, measuring cup NV). The viscosity is measured at 23° C. After activation and rectification of the system, spindle MV is installed. Afterward, the material to be measured is filled into the measuring cup NV. Without undue delay, the spindle is lowered into the measuring cup NV. The spindle should be covered by a layer of at most, one mm. The material to be measured is tempered for 20 min at 23° C. The measurement is started and the viscosity values (mPas) are recorded starting 20 s after the start of measurement. Care must be taken so that measuring cup NV does not rotate or move at all. A value for the viscosity is obtained in mPas. The above mentioned method of measurement corresponds to DIN 53018-1.

The constituents of component A can differ in more parameters than just their viscosity. It is also possible and within the general teaching of the present invention that the constituents differ e.g. in viscosity and chemical constitution.

Generally, the ratio of the amount of constituent with the lowest viscosity to the amount of constituent with the highest viscosity can be chosen relatively freely, depending on the desired properties of the precursors and the cured resin. It has, however, proven to be advantageous when ratio of the amount of constituent with the lowest viscosity to the amount of constituent with the highest viscosity is within a range of from about 1:20 to 20:1, especially 1:10 to 10:1 or 1:5 to 5:1. Good results can be obtained with ratios of from about 1:3 to 3:1 or 1:2 to 2:1. It has furthermore proven adequate in some cases, when the amount of constituent with the highest viscosity is about equal to or higher than the amount of constituent with the lowest viscosity, resulting in a value of from about 0.9:1 to 3:1 for the ratio of the amount of constituent with the highest viscosity to the amount of constituent with the lowest viscosity. All ratios given are based on the weight of the constituents.

Component (B) is preferably an organohydrogenpolysiloxane with at least 3 Si-bonded hydrogen atoms per molecule. This organohydrogenpolysiloxane preferably contains about 0.01 to about 1.7 wt.-% or about 1.0 to about 1.7 wt.-% silicon-bonded hydrogen. The silicon valencies which are not saturated with hydrogen or oxygen atoms are saturated with monovalent hydrocarbon radicals R which, however, are free from ethylenically unsaturated bonds.

The Si-bonded hydrogen atoms per molecule can also be specified in mmol/g. In this respect component (B) contains about 1 to about 8.5 mmol/g silicon-bonded hydrogen or about 2 to about 6 mmol/g silicon-bonded hydrogen.

Component (B) has usually a viscosity in the range of about 15 to about 600 mPas or in the range of about 50 to about 250 mPas.

Component (B) can also comprise more than one, optionally two or three different organohydrogenpolysiloxane constituents (B1, B2, B3).

The hydrocarbon radicals correspond to the radicals R as defined above without the radicals having an ethylenically unsaturated bond. In a preferred embodiment of the present invention, at least 50%, preferably 100% of the hydrocarbon radicals in component B which are bonded to silicon atoms are methyl radicals. Such components are also described in the literature mentioned above with regard to structure and preparation.

Suitable components (C) are organopolysiloxanes without reactive substituents as described e.g. in W. Noll "Chemie and Technologie der Silikone", Verlag Chemie Weinheim, 1968, pages 212 ff. These are preferably linear, branched or cyclic organopolysiloxanes where all silicon atoms are surrounded by oxygen atoms or monovalent hydrocarbon radicals with 1 to 18 carbon atoms which can be substituted or non-substituted. The hydrocarbon radicals can be methyl, ethyl, $C_2$-$C_{10}$ aliphatics, trifluoropropyl groups as well as aromatic $C_6$-$C_{12}$ radicals. Component (C) can contribute to thinning and expanding the rubber network and can act as a plasticizer for the cured material.

Polydimethylsiloxanes with trimethylsiloxy end groups are particularly preferred as component (C). Component (C) is used in the material according to the present invention preferably in an amount of 0 to 40 wt.-%, preferably 0 to 20 wt.-% or 0.1 to 10 wt.-%.

Component (D) is preferably a platinum complex which can be prepared from hexachloroplatinum acid by reduction with tetramethyldivinyldisiloxane. Such compounds are known to the skilled person. Any other platinum compounds which catalyze or accelerate addition cross-linking of silanes with ethylenically unsaturated double bonds are also suitable. Platinum-siloxane complexes as described, e.g. in U.S. Pat. No. 3,715,334, U.S. Pat. No. 3,775,352 and U.S. Pat. No. 3,814,730 are suitable, for example. The disclosure of these patents with regard to platinum complexes and their preparation is explicitly mentioned and expressly regarded as part of the disclosure of the present text and is herein incorporated by reference.

The platinum catalyst is preferably used in quantities of 0.00005 to 0.05 wt.-%, particularly 0.0002 to 0.04 wt.-%, each calculated as elemental platinum and related to the overall weight of the material present with the components (A) to (H).

To control the reactivity of the addition reaction and to prevent premature curing, it may be advantageous to add an inhibitor which prevents the addition reaction for a specific period of time or slows the addition reaction down. Such inhibitors are known and described, e.g. in U.S. Pat. No. 3,933,880, the disclosure of which regarding such inhibitors and their preparation is expressly regarded as being part of the disclosure of the present invention. Examples of such inhibitors are acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based an vinyl siloxane are 1,1,3,3-tetramethyl-1,3-divinyl siloxane and poly-, oligo- and disiloxanes containing vinyl groups. The inhibitor is regarded as a part of component D.

Component (E) is an agent generally capable of giving a hydrophilic character to a composition or a hydrophilizing agent, which reduces the wetting angle of a drop of water or a water containing composition (e.g. a plaster suspension or the like) compared with the original silicon composition not containing component E, and thus promotes a better wettability of the overall composition in the damp mouth region and thus a better flow-on behaviour of the pastes.

The measurement of the wetting angle to determine the hydrophilicity of impression materials is e.g. described in DE 43 06 997 A, page 5, the contents of this document with regard to this method of measurement being expressly mentioned by reference and being regarded as part of the disclosure of the present text.

The hydrophilizing agents are preferably not equipped with reactive groups so that they are not incorporated into the polysiloxane network. Suitable hydrophilizing agents are preferably wetting agents from the group of hydrophilic silicone oils which are not capable of being covalently incorporated into the hardened polymer network. Suitable hydrophilizing agents are described in WO 87/03001 and in EP-B-0 231 420, the contents of which with regard to the hydrophilizing agents is expressly mentioned by reference and is regarded as part of the disclosure of the present invention.

Furthermore, ethoxylized fatty alcohols which are e.g. described in EP-B-0 480 238 are preferred. Furthermore, preferred hydrophilizing agents are polyether carbosilanes, e.g. known from WO 96/08230. Preferred are also the non-ionic perfluoralkylated surface-active substances described in WO 87/03001. Also preferred are the non-ionic surface-active substances which are described in EP-B-0 268 347, i.e. the nonylphenolethoxylates, polyethylene glycol-mono- and diesters, sorbitan esters as well as polyethylene glycol-mono- and diethers listed therein. The contents of the latter documents with regard to hydrophilizing agents and their preparation is expressly mentioned by reference and is regarded as part of the disclosure of the present invention.

The amounts of hydrophilizing agents used is 0 to about 10 wt.-%, relative to the overall weight of all components, preferably 0 to 2 wt.-% and particularly preferably 0.2 to 1 wt.-%. The wetting angle of a drop of water on the surface of a cured material according to the invention measured after 3 minutes, is preferably less than 60°, particularly preferably <50°, in particular <40°.

The compositions of the present invention also include a filler as component F, preferably a mixture of hydrophobic fillers. A wide variety of inorganic, hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4-6, µm); amorphous silicone dioxides, such as a diatomaceous earth (4-7, µm); and silanated fumed silica, such as Cab-o-Sil TS-530 (160-240 $m^2$/g), manufactured by Cabot Corporation.

The sizes and surface areas of the foregoing materials are controlled to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or silazides. Such fillers can be present in amounts of from about 5 to about 65 weight percent, especially about 10 to about 60 or about 20 to about 50 wt.-% of the composition.

Among the fillers which can be used according to component (F) are non-reinforcing fillers such as quarz, cristobalite, calcium silicate, diatomaceous earth, zirconium silicate, montmorillonite such as bentonite, zeolite, including moleculer sieves such as sodium aluminium silicate, metal oxide powder such as aluminium or zinc oxide or their mixed oxides, barium sulphate, calcium carbonate, plaster, glass and plastic powder.

Suitable fillers are also reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than 50 μm.

The overall content of fillers (F) is in the range from 10 to 90%, preferably 30 to 80%, with regard to components A to H.

A combination of reinforcing and non-reinforcing fillers is particularly preferred. In this respect, the quantity of reinforcing fillers ranges from about 1 to about 10 wt.-%, in particular from about 2 to about 5 wt.-%.

The difference in the named overall ranges, i.e. about 9 to about 70 wt.-%, in particular about 28 to about 55 wt.-% is accounted for by non-reinforcing fillers.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Particularly preferred non-reinforcing fillers are quartzes, cristobalites and sodium aluminium silicates which can be surface-treated. The surface treatment can generally be carried out with the same methods as described in the case of the strengthening fillers.

Furthermore, the dental materials according to the invention can optionally contain additives such as plasticizers, pigments, anti-oxidizing agents, release agents and the like as component (G). For example, a chemical system may be employed to diminish the presence or degree of hydrogen outgassing which may be typically generated as a result of the vinyl polymerization. The composition thus may comprise a finely divided platinum metal that scavenges for and takes up such hydrogen. The platinum metal may be deposited upon a substantially insoluble salt having a surface area of between about 0.1 and 40 m²/g. Suitable salts are barium sulphate, barium carbonate and calcium carbonate of suitable particle sizes. Other substrates include diatomaceous earth, activated alumina, activated carbon and others. The inorganic salts are especially preferred to impart improved stability to the resulting materials incorporating them. Dispersed upon the salts is about 0.2 to 2 parts per million of platinum metal, based upon the weight of the catalyst component. It has been found that employment of the platinum metal dispersed upon inorganic salt particles substantially eliminates or diminishes hydrogen outgassing during curing of dental silicones.

The materials according to the invention contain such additives in quantities of 0 to 2 wt.-%, preferably 0 to 1 wt.-%.

The component (H) according to the present invention contains at least one silane compound with at least 2 ethylenically unsaturated groups. Preferred silane compounds follow the general formula II

$$Si(R^1)_n(R^2)_{4-n} \quad (II)$$

wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups or have a detrimental influence on such a reaction with 1 to 12 carbon atoms and n is 2, 3 or 4. Especially preferred radicals $R^1$ are vinyl, allyl and propargyl, especially preferred radicals $R^2$ are linear or branched $C_1$-$C_{12}$ alkyl groups.

Further preferred silane compound follow the general formula III:

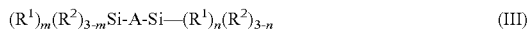

$$(R^1)_m(R^2)_{3-m}Si\text{-}A\text{-}Si\text{-}(R^1)_n(R^2)_{3-n} \quad (III)$$

wherein $R^1$ and $R^2$ and n are independently from each other defined as above, a is a bivalent linear or branched or alicyclic, heterocyclic, aromatic or heteroaromatic group with 1 to 10000 carbon atoms which can contain nitrogen or oxygen atoms and m is 2 or 3, preferably 3. Examples for bivalent radicals A are ethylene, propylene, butylene, penylene, hexylene, heptylene, octylene, nonylene, decylene, —$H_2C$—Ar—$CH_2$—, —$C_2H_4$—Ar—$C_2H_4$— with Ar being an aromatic bivalent radical, preferably phenyl, or bivalent polyether radicals of the general type —$CH_2CH_2CH_2$—O—[$C_aH_{2a}O$]$_b$—$CH_2CH_2CH_2$— with $1 \leq a \leq 5$ and $0 \leq b \leq 2000$.

Also suitable as component H are silane dendrimers. Generally, there-dimensional, highly-ordered oligomer and polymer compounds are described as dendrimers, which are synthesized starting from small core molecules by a constantly repeating sequence of reactions. Monomer or polymer molecules with at least one reactive site are suitable as a core molecule. This is converted in a uni- or multi-level reaction with a reactant which accumulates at the reactive site of the core molecule and for its part has two new reactive sites. The conversion of core molecule and reactant yields the core cell (generation zero). By repeating the reaction, the reactive sites in the first reactant layer are converted with further reactants, again at least two new branching sites being introduced into the molecule each time (1$^{st}$ generation).

The progressive branching leads to a geometrical growth of the number of atoms for each generation. As the overall size can only grow linearly because of the number of possible covalent bonds specified by the reactants, the molecules become more tightly packed from generation to generation and they change their shape from starfish-shaped to spherical. Dendrimers of the zero and each further generation can be dendrimers used as component (H) according to the Invention. Preferred are those of the first generation although those of much higher generations can be used.

Dendrimers of the first or higher generations are obtained as a core molecule by conversion of tri- or tetraalkenyl silanes (preferably allyl and vinyl) in a first step with hydrogenchloro-silanes. These products are converted in a further step with alkenyl-Grignard compounds.

Particularly preferred in this case are dendrimers of the first generation of the following formula IV:

$$SiR^2_x((CH_2)_n\text{—}Si\text{—}((CH_2)_m\text{—}CH\text{=}CH_2)_3)_{4-x} \quad (IV)$$

in which $R^2$ is defined as above, n=2, 3, 4 or 5, m=0, 1, 2 or 3, and x=0 or 1.

Particularly preferred dendrimers according to general formula (IV) are:

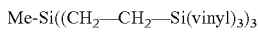
Me-Si((CH$_2$—CH$_2$—Si(vinyl)$_3$)$_3$

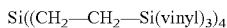
Si((CH$_2$—CH$_2$—Si(vinyl)$_3$)$_4$

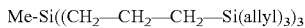
Me-Si((CH$_2$—CH$_2$—CH$_2$—Si(allyl)$_3$)$_3$

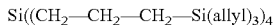
Si((CH$_2$—CH$_2$—CH$_2$—Si(allyl)$_3$)$_4$

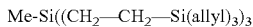
Me-Si((CH$_2$—CH$_2$—Si(allyl)$_3$)$_3$

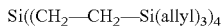
Si((CH$_2$—CH$_2$—Si(allyl)$_3$)$_4$

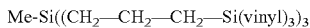
Me-Si((CH$_2$—CH$_2$—CH$_2$—Si(vinyl)$_3$)$_3$

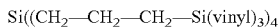
Si((CH$_2$—CH$_2$—CH$_2$—Si(vinyl)$_3$)$_4$

A. W. van der Made and P. W. N. M. van Leeuwen describe the main synthesis of those silane dendrimers in J. Chem. Soc. Commen. (1992), page 1400 and in Adv. Mater. (1993), 5, no. 6, pages 366 ff. The Synthesis begins for example with complete allylation of tetrachlorosilane to tetraallylsilane using 10% excess of allyl magnesium bromide in diethyl ether. In addition, the allyl groups are hydrosilylized with trichlorosilane in the presence of a platinum catalyst.

Finally, the conversion takes place with allyl magnesium bromide in diethyl ether. As a result, a dendrimer is obtained with 12 allyl end groups. This first generation can also be converted to a second generation, 36 allyl groups being obtained. The Same topic is also dealt with by D. Seyferth lo and D. Y Son in Organometallics (1994), 13, 2682-2690.

Conversion products of tri- or tetra- or penta- or hexa- or hepta- or octaalkenyl(cyclo)siloxanes with hydrogenchlorosilanes are furthermore possible as a core molecule. These are converted in a further step with alkenyl-Grignard compounds and lead to dendrimers with cyclical or linear siloxane cores.

Both purified tri-, tetra-, penta-, hexa-, hepta- or octasiloxane dendrimers as well as any mixtures of those dendrimers can be used according to the Invention.

Silane dendrimers, the preparation and use as varnishes of which are known from DE-A-196 03 242 and 195 17 838 as well as from EP-A-0 743 313. Dendrimers listed there are also suitable for the purpose according to the Invention. Polyfunctional alkenyl compounds are furthermore suitable as cores.

Particularly suitable are trimethylolpropanetriallylether, tetrallylpentaerythrite, Santolink XI-100 (Monsanto), tetraallyloxyethane, 1,3,5-benzoltricarbonic acid triallyl ester, 1,2,4-benzoltricarbonic acid triallylester, 1,2,4,5-benzoltetracarbonic acid tetrallylester, triallyl phosphate, triallyl citrate, Manyl isocyanurate, triallyloxytriazine, hexaallylinosite, as well as general compounds which possess at least two ethylenically unsaturated groups which can be optionally substituted, for example, o-allyl, n-allyl, o-vinyl, n-vinyl or p-vinylphenolether groups.

Possible polyenes are also described in U.S. Pat. No. 3,661,744 and EP-A-0 188 880. The polyene can have e.g. the following structure: (Y)—(X)$_m$, where m is an integer greater than or equal to 2, preferably 2, 3 or 4, and X is chosen from —[RCR]$_f$, —CR=CRR, —O—CR=CR—R, —S—CR=CR—R, —NR—CR=CR—R group, f is an integer from 1 to 9 and the R radicals having the meanings H, F, Cl, furyl, thienyl, pyridyl, phenyl and substituted phenyl, benzyl and substituted benzyl, alkyl and substituted alkyl, alkoxy and substituted alkoxy as well as cycloalkyl and substituted cycloalkyl and each being able to be the same or different. (Y) is an at least difunctional organic radical which is constructed from atoms which are chosen from the C, O, N, Cl, Br, F, P, Si and H group.

The allyl- and/or vinyl esters of the at least difunctional carbonic acids are for example very suitable polyene compounds. Suitable carbonic acids for this are those with carbon chains of 2 to 20 C atoms, preferably 5 to 15 C atoms. Allyl or vinyl esters of aromatic dicarbonic acids such as phthalic acid or trimellithic acid are also very suitable. Allyl ethers of polyfunctional alcohols, preferably at least trifunctional alcohols are also suitable. Allyl ethers of trimethyl propane, pentaerythrite Manyl ether or 2,2-bis-oxyphenylpropane-bis-(diallyl phosphate) can be named as examples. Compounds of the cyanuric acid triallylester, Manyl triazintrione type and similar are also suitable.

Dendrimers of the above mentioned type and their preparation are described in U.S. Pat. No. 6,335,413 B1. The disclosure of this document with regard to such dendrimers and their preparation is expressly regarded as part of the disclosure of the present invention and is herein incorporated by reference.

In a further preferred embodiment of the present invention, compounds of the general formula II or III or their mixtures are used as component H. Preferably compounds of the general formula II where n is 3 or 4, especially 4 and radicals R$^1$ are vinyl, allyl and propargyl and radical R$^2$ is methyl or ethyl are used.

For dental applications component (H) would be present in quantities of from 0.01 to 10 wt.-%, preferably 0.05 to 5 wt.-% or 0.1 to 1 wt.-%. Even the addition of very small amounts of component (H) effects a considerable increase in the tear strength of impression materials. In a preferred embodiment, component H is present in the dental materials in an amount of 0.1 to about 2 wt.-%, e.g. 0.15 to less than 1 wt.-%.

The quantity of components (A), (B) and (H) are preferably chosen such that 0.5 to 10 mol SiH units of component (B) are present per mol of unsaturated double bond of components (A) and (H). The amount of components (A), (H), and the (B) in the dental material is in the range of from 5 to 70 wt.-% relative to the total weight of all components. Preferably, the amount is in the range of from 10 to 60 wt.-% and particularly in a range of from 15 to 50 wt.-%.

The materials according to the present invention are prepared by mixing the components (A) to (H) and subsequently curing them in an addition reaction designated as hydrosilylizing in which, under the influence of the platinum catalyst (D), the SiH groups of the component (B) are added to the unsaturated groups of the components (A) and (H) respectively.

In a preferred embodiment the material according to the present invention comprises:
  5-70 wt.-% components (A), (B) and (H) combined,
  0-40 wt.-% component (C),
  0.00005-0.05 wt.-% component (D), calculated as elemental platinum and relative to the combined weight of compounds (A) to (H),
  0-10 wt.-% component (E),
  10-90 wt.-% component (F),
  0-5 wt.-% component (G), and
  0.1-50 wt.-% component (H).

In another preferred embodiment the material according to the present invention comprises:
  10-60 wt.-% components (A), (B) and (H) combined,
  0-20 wt.-% component (C),
  0.0002-0.04 wt.-% component (D), calculated as elemental platinum and relative to the combined weight of compounds (A) to (H),
  0-2 wt-% component (E),
  30-80 wt.-% component (F),
  0-2 wt.-% component (G), and
  0.1-20 wt.-% component (H).

For reasons of storage stability, it is preferable to formulate the materials in a two-component dosage form in which the overall component (B) is present in a so-called base paste. The overall component (D) is present physically separated from the base paste in a so-called catalyst paste. The components (A) or (H) or both can be either present in the catalyst or base paste, respectively, preferably a part of each of components (A) and (H) respectively being present in the base paste and a part of components (A) or (H) in the catalyst paste.

The present invention thus also relates to a material according to the present invention, wherein said material is present in the form of a base paste and a catalyst paste physically separated from it, the whole component (B) being present in the base paste and the whole component (D) being present in the catalyst paste and the remaining components being optionally distributed in the two pastes.

The components (C), (E), (F) and (G) can be present in their full amount in the catalyst or base paste, where it is preferable that a part of each of the respective components are present in the catalyst paste and a part in the base paste.

The volume ratios of catalyst and base pastes can be 10:1 to 1:10. Particularly preferred volume ratios of base paste:catalyst paste are about 1:1 and about 5:1 (5 parts base paste:1 part catalyst paste). In the case of a volume ratio of 1:1, the components (A) to (H) can be distributed as follows as base and catalyst paste.

TABLE 1

| Component | Base paste (wt.-%) | Catalyst paste (wt.-%) | Total in base and catalyst paste (wt.-%) |
|---|---|---|---|
| (A) | 0-60 | 0-60 | 0-60 |
| (B) | 2-60 | — | 1-30 |
| (C) | 0-20 | 0-20 | 0-20 |
| (D) | — | 0.0001-0.1 | 0.00005-0.05 |
| (E) | 0-10 | 0-10 | 0-10 |
| (F) | 10-90 | 10-90 | 10-90 |
| (G) | 0-4 | 0-4 | 0-2 |
| (H) | 0-50 | 0-50 | 0.1-50 |

In the case of a volume ratio of 5 parts base paste to 1 part catalyst paste, preferred quantity ratios can be used as follows:

TABLE 2

| Component | Base paste (wt-%) | Catalyst paste (wt.-%) | Total in base and catalyst paste (wt.-%) |
|---|---|---|---|
| (A) | 0-60 | 0-60 | 0-60 |
| (B) | 1.2-36 | — | 1-30 |
| (C) | 0-24 | 0-20 | 0-20 |
| (D) | — | 0.00025-0.25 | 0.00005-0.05 |
| (E) | 0-10 | 0-10 | 0-10 |
| (F) | 10-90 | 5-90 | 10-90 |
| (G) | 0-2.4 | 0-4 | 0-2 |
| (H) | 0-10 | 0-10 | 0.01-10 |

With a volume ratio 5:1, both pastes can be filled into tubular film bags and later, shortly before use, can be mixed using a mixing and dosing device auch as PENTAMIX® mixing machine (available from 3M ESPE AG).

A dosage in the form of double-chambered cartridges or capsules is also possible.

The compounds according to the present invention are generally obtainable by mixing the respective components in the amounts given above.

The present invention thus also relates to a method for the preparation of a material according to the present invention, wherein components A, B, D, F, H and optionally one or more of components C, E and G are mixed.

The present invention als relates to a method for the preparation of a material in a two component dosage, wherein component B and one or more of components A, C and E to H are mixed to form a base paste and component D and one or more of components A, C and E to H are mixed to form a catalyst paste.

The materials according to the present invention are particularly suitable as dental materials and are characterized by an unusually good tear strength between about 2.1 and about 6 MPa, or between about 2.2 to about 5 MPa, especially between about 2.4 and about 4 MPa. It has, however, been found to be advantageous, if the tear strength does not exceed a value of more than about 8 MPa. Generally, values for the tear strength between about 2.1 and 3.5 MPa, especially between about 2.4 and 3.2 MPa provide for a smooth removability of the imprint after curing, yet preserving the details of the preparation.

The Materials according to the invention have an end hardness of preferably shore hardness A$\geq$40, preferably ÷45, particularly preferably shore hardness A$\geq$50 with excellent low processing viscosity and non-dripping consistency. The upper limit for the shore A hardness of the cured materials according to the present invention is at a value of about 70, or about 65.

The materials according to the present invention exhibit an improved elasticity, measurable by an elongation of at least about 50%, preferably of at least about 70%. The upper limit for the elongation of the materials according to the present invention is about 300%, preferably less than about 250% or less than about 200%.

It is also a preferred feature of the materials according to the present invention that their consistency according to ISO 4823 is greater than 36 mm, preferably greater than 37 mm or greater than 38 mm or greater than 40 mm. Most preferred materials according to the present invention exhibit a consistency of more than 41 mm, e.g., between 42 and 48 mm. The upper limit for the consistency according to ISO 4823 is about 50 mm.

The materials according to the present invention also show an improved dripping behavior, since due to the freedom in formulation the rheological behavior can be controlled over a wide range. It is preferred that uncured, but mixed precursor materials according to the present invention have a dripping behavior (dripping consistency) which is at least sufficient, according to the method of measurement described herein.

The present invention thus also relates to the use of a curable material comprising:
(A) at least two different types of organopolysiloxanes A1 and A2 with at least two ethylenically unsaturated groups per molecule,
(B) organohydrogenpolysiloxanes with at least 3 SiH groups per molecule,
(C) optionally organopolysiloxanes without reactive groups,
(D) a catalyst for promoting the reaction between A and B,
(E) optionally hydrophilizing agents,
(F) fillers,
(G) optionally conventional dental additives, adjuvants and colorants,
(H) at least one silane with at least two alkenyl groups per molecule wherein the at least two different types of organopolysiloxanes A1 and A2 with at least two ethylenically unsaturated groups per molecule have a different viscosity and the consistency of the curable material according to ISO 4823 is >35 mm, for the preparation of impression materials in dental applications.

The invention is explained in further detail by the following examples.

EXAMPLES

In the following examples several base and catalyst pastes were formulated to show the effect of tetraallylsilane and the combination of organopolysiloxanes on tear strength, hardness and consistency of the materials.

Example A

Component A

| Compound | amount [wt.-%] |
|---|---|
| Vinyl terminated Polydimethylsiloxane, 200 cSt | 19.250 |
| Vinyl terminated Polydimethylsiloxane, 7000 cSt | 24.750 |
| Polymethylhydrogensiloxane (1.78 mmol/g SiH, 50 cSt) | 6.000 |
| Polymethylhydrogensiloxane (4.00 mmol/g SiH, 100 cSt) | 7.000 |
| Polydimethylsiloxane, 10 cSt | 7.000 |
| Hydrophobized fumed silica (100 m$^2$/g) | 4.000 |
| Hydrophobized cristobalit filler (average particle size: 3 μm) | 29.500 |
| Yellow pigment | 0.500 |
| Polyether surfactant | 1.500 |
| Tetraallylsilane | 0.500 |

Example B

Component A

| Compound | amount [wt.-%] |
|---|---|
| Vinyl terminated Polydimethylsiloxane, 200 cSt | 19.750 |
| Vinyl terminated Polydimethylsiloxane, 7000 cSt | 24.750 |
| Polymethylhydrogensiloxane (1.78 mmol/g SiH, 50 cSt) | 6.000 |
| Polymethylhydrogensiloxane (4.00 mmol/g SiH, 100 cSt) | 7.000 |
| Polydimethylsiloxane, 10 cSt | 7.000 |
| Hydrophobized fumed silica (100 m$^2$/g) | 4.000 |
| Hydrophobized cristobalit filler (average particle size: 3 μm) | 29.500 |
| Yellow pigment | 0.500 |
| Polyether surfactant | 1.500 |

Example C

Component A

| Compound | amount [wt.-%] |
|---|---|
| Vinyl terminated Polydimethylsiloxane, 200 cSt | 19.000 |
| Vinyl terminated Polydimethylsiloxane, 7000 cSt | 24.750 |
| Polymethylhydrogensiloxane (1.78 mmol/g SiH, 50 cSt) | 6.000 |
| Polymethylhydrogensiloxane (4.00 mmol/g SiH, 100 cSt) | 7.000 |
| Polydimethylsiloxane, 10 cSt | 7.750 |
| Hydrophobized fumed silica (100 m$^2$/g) | 4.000 |
| Hydrophobized cristobalit filler (average particle size: 3 μm) | 29.500 |
| Yellow pigment | 0.500 |
| Polyether surfactant | 1.500 |

Example D

Component A

| Compound | amount [wt.-%] |
|---|---|
| Vinyl terminated Polydimethylsiloxane, 200 cSt | 10.000 |
| Vinyl terminated Polydimethylsiloxane, 7000 cSt | 15.750 |
| Vinyl terminated Polydimethylsiloxane, 1000 cSt | 18.000 |
| Polymethylhydrogen siloxane, (1.78 mmol/g Si-H; 50 cSt) | 6.000 |
| Polymethylhydrogen siloxane, (4.0 mmol/g Si-H; 100 cSt) | 7.000 |
| Hydrophobized fumed silica (100 m$^2$/g) | 4.000 |
| Hydrophobized cristobalit filler (average particle size: 3 μm) | 29.500 |
| Yellow pigment | 0.500 |
| Polyether surfactant | 1.500 |
| Tetraallylsilane | 0.750 |

Example E

Component B

| Compound | amount [wt.-%] |
|---|---|
| Vinyl terminated Polydimethylsiloxane, 200 cSt | 13.500 |
| Vinyl terminated Polydimethylsiloxane, 7000 cSt | 28.000 |
| Polydimethylsiloxane, 10 cSt | 5.000 |
| Critoballit filler (average particle size: 3 μm) | 50.000 |
| Hydrophobized fumed silica (100 m$^2$/g) | 2.600 |

Example F

Component B

| Compound | amount [wt.-%] |
|---|---|
| Vinyl terminated Polydimethylsiloxane, 200 cSt | 13.641 |
| Vinyl terminated Polydimethylsiloxane, 7000 cSt | 27.778 |
| Polydimethylsiloxane, 10 cSt | 4.216 |
| Hydrophobized fumed silica (100 m$^2$/g) | 2.579 |
| Hydrophobized cristobalit filler (average particle size: 3 μm) | 49.603 |
| Yellow pigment | 0.099 |
| Platinum catalyst solution | 1.578 |
| Tetraallylsilane | 0.496 |

Example G

Component B

| Compound | amount [wt.-%] |
|---|---|
| Vinyl-terminated Polydimethylsiloxane, 1000 cSt | 29.000 |
| Vinyl-terminated Polydimethylsiloxane, 7000 cSt | 12.500 |
| Polydimethylsiloxane, 10 cSt | 5.000 |
| Cristoballit filler (Average particle size: 3 μm) | 50.000 |

-continued

| Compound | amount [wt.-%] |
|---|---|
| Hydorphobized fumed similca (100 m²/g) | 2.600 |
| Yellow Pigment 0.100 | 0.100 |
| Platinum catalyst solution | 0.800 |

Results:

| Combination | | Tear Strength | Shore Hardness A |
|---|---|---|---|
| Component A | Component B | (24 h) [Mpa] | 10 min/24 h |
| Example A | Example E | 2.97 | 54/57 |
| Example B | Example E | 2.02 | 45/45 |
| Example C | Example F | 2.80 | 55/60 |
| Example D | Example G | 2.5 | 56/59 |

These experimental pastes were mixed with a static mixer in a volume ratio of 1:1 (base and catalyst paste) after filling into a standard cartridge.

Measurements:

Tear Strength:

Tear strength was measured by tearing six dumbbell-shaped specimen in a Zwick 1435 Universal testing machine according to B 6×50 DIN 50125. The diameter of the samples was 6 mm and their length 50 mm. Base and catalyst pastes were mixed through a static mixer and filled into a brass mold. After 24 hours at 23° C. the specimen were removed, six measurements were made and the mean value determined.

Setting Times:

Setting time data are given for room temperature and evaluated using a Shawburry Curometer. The end of the setting time was defined as the time after which the curing curve fell below the 10 mm line.

For determining the dripping behaviour of Type 3 Silicone Materials, 1.0±0.2 g material is mixed and dosed into a standard konvex shaped glass plate (d=60 mm). The material is automixed in special cartridges (v/v=1:1) and special static mixing tips. The material must form a circle shaped contact area with the glass at an average diameter of 15±1 mm. 15 s after mixing, the glass plate with the material is fixed in an upside down position so that the material can drop down. The amount of dripping material is measured. 0% is rated (+); >0%<20% is rated (0); >20% is rated (−).

Tear Strength and Maximum Elongation

Results:

| Combination | | Tear strength | Shore hardness A (DIN | Consistency | Setting time | Dripping |
|---|---|---|---|---|---|---|
| Base paste | Catalyst paste | (24 h) MPa | 53505) 10 min/24 h | ISO 4823 [mm] | [min:sec] | consistency |
| Imprint II low Viscosity Regular Set[a] | | 1.5 | 52/56 | 41 | | 0 |
| Dimension Garant[b] L | | 1.6 | 44/45 | 42 | | + |
| Aquasil XLV[c] | | 3.2 | 35/36 | 46 | | − |
| A | E | 3.0 | 54/57 | 44 | 5:20 | + |
| B | E | 2.0 | 45/45 | 46 | 4:30 | + |
| C | F | 2.8 | 55/60 | 43 | 4:30 | + |

[a]includes no tetraallylsilane
[b]includes no tetraallylsilane
[c]includes VQM-resin The commercially available materials and the combination B/E are not examples according to the invention.

The results show that the inventive materials offer a unique combination of tear strength, shore hardness and consistency not to be found in the prior art.

The invention claimed is:

1. A curable material comprising:
   component (A) comprising at least two different types of organopolysiloxanes, (A1) having a viscosity value of 10 to 1,000 mPa-s, and (A2) having a viscosity value of 500 to 45,000 mPa-s, with at least two ethylenically unsaturated groups per molecule;
   component (B) comprising organohydrogenpolysiloxane with at least three SiH groups per molecule;
   component (D) comprising a catalyst for promoting the reaction between (A) and (B);
   component (F) comprising filler; and
   component (H) comprising at least one silane with at least two alkenyl groups per molecule,
   wherein the consistency of the curable material according to ISO 4823 is greater than 40 mm.

2. The material according to claim 1, wherein the viscosity of at least one of the organopolysiloxanes of component (A) is at least twice the viscosity of another organopolysiloxane of component (A).

3. The material according to claim 1 comprising:
   5-70 wt.-% components (A), (B), and (H) combined;
   0-40 wt.-% organopolysiloxane without reactive groups;
   0.00005-0.05 wt.-% catalyst (D), calculated as elemental platinum and relative to the total weight of the material;
   0-10 wt.-% hydrophilizing agents;
   10-90 wt.-% component (F);
   0-5 wt.-% conventional dental additives, adjuvants and colorants; and
   0.1-50 wt.-% component (H).

4. The material according claim 3 comprising:
   10-60 wt.-% components (A), (B), and (H) combined;
   0-20 wt.-% organopolysiloxane without reactive groups;
   0.0002-0.04 wt.-% catalyst (D), calculated as elemental platinum and relative to the overall weight of the material;
   0-2 wt-% hydrophilizing agent;
   30-80 wt.-% component (F);
   0-2 wt.-% conventional dental additives, adjuvants and colorants; and
   0.1-20 wt.-% component (H).

5. The material according claim 1, wherein the quantities of components (A), (B) and (H) are selected such that 0.5 to 10 mol SiH units in component (B) are present per mol of unsaturated double bond in components (A) and (H).

6. The material according to claim 1 wherein, said material is prepared from two pasty compositions in the form of a base paste and a catalyst paste, wherein the entire amount of said organohydrogenpolysiloxane is present in the base paste, and the entire amount of said catalyst is present in the catalyst paste, and the remaining components are distributed between the two pastes.

7. The material according to claim 6, wherein the volume ratio of base paste to catalyst paste in the material is 10:1 to 1:10.

8. The material according to claim 1, wherein component A comprises at least three different types of organopolysiloxanes, each with a different viscosity and one organopolysiloxane has a higher viscosity than the other two.

9. The material according to claim 1, wherein the curable material is a dental impression material.

10. A curable material comprising:
component (A) comprising at least two different types of organopolysiloxanes, (A1) having a viscosity value of 10 to 1,000 mPa-s, and (A2) having a viscosity value of 500 to 45,000 mPa-s, with at least two ethylenically unsaturated groups per molecule, with the proviso that the component (A) siloxanes do not comprise aromatic groups;
component (B) comprising organohydrogenpolysiloxane with at least three SiH groups per molecule;
component (D) comprising a catalyst for promoting the reaction between (A) and (B);
component (F) comprising filler; and
component (H) comprising at least one silane with at least two alkenyl groups per molecule,
wherein the consistency of the curable material according to ISO 4823 is greater than 40 mm; and
wherein, upon curing, the material has a Shore A hardness of no greater than about 70.

11. The material according to claim 10, wherein the curable material is a dental impression material.

12. A curable material comprising:
component (A) comprising at least two different types of organopolysiloxanes, (A1) having a viscosity value of 10 to 1,000 mPa-s, and (A2) having a viscosity value of 500 to 45,000 mPa-s, with at least two ethylenically unsaturated groups per molecule;
component (B) comprising organohydrogenpolysiloxane;
component (D) comprising a catalyst for promoting the reaction between (A) and (B);
component (F) comprising filler; and
component (H) comprising at least one silane with at least two alkenyl groups per molecule
wherein the consistency of the curable material according to ISO 4823 is greater than 40 mm;
wherein, upon curing, the material has an elongation at break value of 70 to 300%.

13. The curable material of claim 12, wherein, upon curing, the material has a Shore A hardness of no greater than about 70.

14. A curable material comprising:
component (A) consisting of two different types of organopolysiloxanes, (A1) having a viscosity value of 10 to 1,000 mPa-s, and (A2) having a viscosity value of 500 to 45,000 mPa-s, with at least two ethylenically unsaturated groups per molecule, with the proviso that the component (A) siloxanes do not comprise aromatic groups;
component (B) comprising organohydrogenpolysiloxane with at least three SiH groups per molecule;
component (D) comprising a catalyst for promoting the reaction between (A) and (B);
component (F) comprising filler; and
component (H) comprising at least one silane with at least two alkenyl groups per molecule; wherein said at least one silane is selected from the group consisting of compounds that can be represented by the general formula (II)

$$Si(R1)_n(R2)_{4-n} \qquad (II)$$

wherein R1 is a linear, branched or cyclic monovalent ethylenically unsaturated substituent which can undergo an addition reaction with SiH-groups, having from 2 to 12 carbon atoms, R2 is a monovalent radical without groups that can undergo an addition reaction with SiH-groups and n is 2, 3 or 4,
wherein the consistency of the curable material according to ISO 4823 is greater than 40 mm.

15. The curable material of claim 14, wherein, upon curing, the material has a Shore A hardness of no greater than about 70.

16. The curable material of claim 14, wherein component A comprises at least three different types of organopolysiloxanes, each with a different viscosity and one organopolysiloxane has a higher viscosity than the other two.

* * * * *

UNITED STATES PATENT AND TRADEMARK OFFICE
CERTIFICATE OF CORRECTION

PATENT NO. : 8,067,496 B2  
APPLICATION NO. : 13/046068  
DATED : November 29, 2011  
INVENTOR(S) : Zech et al.

Page 1 of 2

It is certified that error appears in the above-identified patent and that said Letters Patent is hereby corrected as shown below:

<u>Pane 2, Column 2 (Other Publications)</u>  
Line 33                Delete "Weinham," and insert -- Weinheim, --, therefor.

<u>Column 2</u>  
Lines 63-64            Delete "consituents." and insert -- constituents. --, therefor.

<u>Column 3</u>  
Lines 5-6              Delete "impression" and insert -- impression. --, therefor.  
Line 29                Delete "the these" and insert -- these --, therefor.  
Line 33                Delete "consituents" and insert -- constituents --, therefor.

<u>Column 4</u>  
Line 52                Delete "consituents" and insert -- constituents --, therefor.  
Line 55                Delete "subsituent" and insert -- substituent --, therefor.  
Line 55                Delete "consituents" and insert -- constituents --, therefor.  
Line 67                Delete "tert.butyl," and insert -- tert-butyl, --, therefor.

<u>Column 5</u>  
Line 19                Delete "2." and insert -- 2nd --, therefor.  
Line 32                Delete "the be" and insert -- be the --, therefor.  
Line 50                Delete "polydipersity" and insert -- polydispersity --, therefor.

<u>Column 8</u>  
Line 9                 Delete "an" and insert -- on --, therefor.  
Line 17                Delete "silicon" and insert -- silicone --, therefor.  
Line 41                Delete "perfluoralkylated" and insert -- perfluoroalkylated --, therefor.  
Line 62                Delete "silicone" and insert -- silicon --, therefor.  
Line 63                Delete "silicone" and insert -- silicon --, therefor.  
Line 64                Delete "silicone" and insert -- silicon --, therefor.

Signed and Sealed this  
Seventh Day of February, 2012

David J. Kappos  
*Director of the United States Patent and Trademark Office*

CERTIFICATE OF CORRECTION (continued)

U.S. Pat. No. 8,067,496 B2

Column 10
Line 27 (Approx.)         Delete "penylene," and insert -- phenylene, --, therefor.
Lines 54-55 (Approx.)     Delete "Invention." and insert -- invention. --, therefor.

Column 11
Line 39 (Approx.)         Delete "Invention." and insert -- invention. --, therefor.
Line 42 (Approx.)         Delete "Invention." and insert -- invention. --, therefor.

Column 12
Line 6                    Delete "trimellithic" and insert -- trimellitic --, therefor.
Line 11                   Delete "triazintrione" and insert -- triazinetrione --, therefor.

Column 13
Line 59                   Delete "auch" and insert -- such --, therefor.

Column 14
Line 3                    Delete "als" and insert -- also --, therefor.
Line 21                   Delete "÷45," and insert -- $\geq 45$, --, therefor.

Column 15
Line 25 (Approx.)         Delete "cristobalit" and insert -- cristobalite --, therefor.
Line 44 (Approx.)         Delete "cristobalit" and insert -- cristobalite --, therefor.
Line 63 (Approx.)         Delete "cristobalit" and insert -- cristobalite --, therefor.

Column 16
Line 15 (Approx.)         Delete "cristobalit" and insert -- cristobalite --, therefor.
Line 32 (Approx.)         Delete "Critoballit" and insert -- Cristobalite -- therefor.
Line 48 (Approx.)         Delete "cristobalit" and insert -- cristobalite --, therefor.
Line 66 (Approx.)         Delete "Cristoballit" and insert -- Cristobalite --, therefor.

Column 17
Line 5 (Approx.)          Delete "Hydorphobized fumed similca" and insert -- Hydrophobized fumed silica --, therefor.
Line 34                   Delete "Shawburry" and insert -- Shawbury --, therefor.

Column 18
Line 38                   In Claim 4, after "according" insert -- to --.

Column 19
Line 1                    In Claim 5, after "according" insert -- to --.